United States Patent [19]

Ruetman

[11] 3,957,781

[45] May 18, 1976

[54] PROCESS FOR PREPARING RING-PERCHLORINATED PYRAZINE-ISOCYANATES

[75] Inventor: Sven H. Ruetman, Walnut Creek, Calif.

[73] Assignee: The Dow Chemical Company, Midland, Mich.

[22] Filed: Feb. 6, 1974

[21] Appl. No.: 440,216

Related U.S. Application Data

[62] Division of Ser. No. 258,074, May 30, 1972, abandoned.

[52] U.S. Cl. .................. 260/250 BN; 260/256.4 N; 260/294.9; 260/296 C; 260/453 P; 260/465 R
[51] Int. Cl.² ...................................... C07D 241/20
[58] Field of Search ....... 260/250 BN, 250 R, 453 P

[56] References Cited
UNITED STATES PATENTS

| | | |
|---|---|---|
| 2,442,473 | 6/1948 | Sayward et al. ................. 260/250 R |
| 3,118,925 | 1/1964 | Mukaiyama et al. ............. 260/453 P |
| 3,390,164 | 6/1968 | Kaplan et al. .................... 260/453 P |
| 3,652,637 | 3/1972 | Bimbor ......................... 260/250 BN |

*Primary Examiner*—Richard J. Gallagher
*Attorney, Agent, or Firm*—J. Roger Lochhead; Robert R. Stringham

[57] ABSTRACT

The invention comprises a process for producing ring-perchlorinated aromatic carbocyclic and N-heterocyclic isocyanates by the vapor phase chlorination of the corresponding acetamido-substituted carbocycle or N-heterocycle. The resulting isocyanate may be further reacted with an active hydrogen-containing compound to form the corresponding carbamate, thiocarbamate, urea, or the like. The invention further comprises certain novel compounds made by such process, said compounds being useful as intermediates for plastic materials or as fine retardant additives in plastics.

6 Claims, No Drawings

PROCESS FOR PREPARING RING-PERCHLORINATED PYRAZINE-ISOCYANATES

CROSS REFERENCE TO RELATED APPLICATION

This is a division of application Ser. No. 258,074 filed May 30 1972 now abandoned.

BACKGROUND OF THE INVENTION

U.S. Pat. No. 3,277,138 discloses a two-step process for chlorinating aromatic carbocyclic isocyanates by first chlorinating the isocyanate at a temperature of from −20° to 150°C. in the absence of the catalyst, and then further chlorinating the resulting product at from 210°–250°C. in the presence of the catalyst. This process, however, has the disadvantage of being long and time-consuming.

SUMMARY OF THE INVENTION

Ring-perchlorinated aromatic carbocyclic and N-heterocyclic isocyanates may be prepared by rapidly and turbulently contacting the prevaporized corresponding acetamido-substituted carbocycle or N-heterocycle with an excess of chlorine at a temperature of from about 500°–650°C. for from about 1–50 seconds.

Optionally, the isocyanate so prepared may be reacted with an active hydrogen-containing compound to produce the corresponding carbamate, thiocarbamate, urea, or the like.

The invention further comprises novel ring-perchlorinated N-heterocyclic isocyanates of one of the formulas

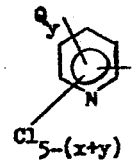
I.

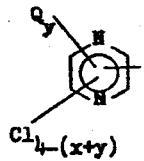
II.

or 
III.

wherein $x$ is 1 or 2; each Q is, independently, CN, F, or $CF_3$; and $y$ represents the number of said substituents remaining after chlorination, i.e., 0 to 2.

The above N-heterocyclic isocyanates are useful as intermediate materials for the manufacture of plastics, such as polyurethanes, or they may be trimerized to the cyanuric acid derivative, which is useful as a fire retardant additive for plastic materials.

DETAILED DESCRIPTION OF THE INVENTION

Suitable starting materials include aromatic carbocyclic and N-heterocyclic compounds which contain one or two acetamido substituents. They are generally available or may be easily synthesized by acetylating the corresponding amine or diamine. In addition to the acetamido, they may contain a total of up to and including two ring substituents such as methyl, nitro, chloro, fluoro, bromo, iodo, cyano, methoxy, $CCl_3$, $CF_3$ and the like. Generally speaking, the chlorination conditions of the present invention will remove all of the foregoing substituents with the exception of F, CN and $CF_3$. It is believed that the acetamido moiety undergoes chlorination, chlorinolysis of the resulting $CCl_3$ moiety and dechlorination to the thermally stable isocyanate group, in conjunction with ring perchlorination involving replacement reactions for the unstable substituents. Suitable starting materials are of the general formulas

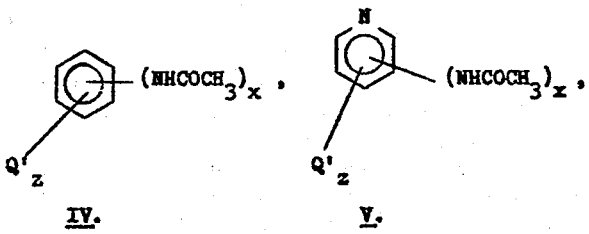
IV.   V.

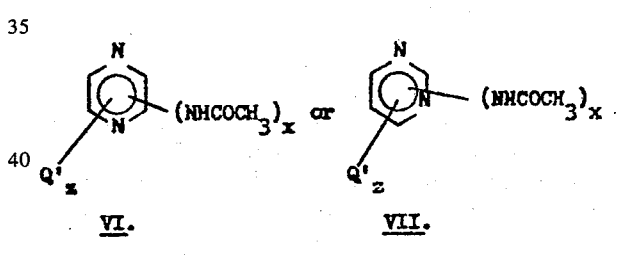
VI.   VII.

wherein $x$ is 1 or 2, $z$ is 0 to 2, and each Q' is, independently, methyl, nitro, chloro, fluoro, bromo, iodo, cyano, methoxy, $CCl_3$, $CF_3$, and the like. While temperatures in the range of about 500°–650°C. are operable, about 550°–600°C. is preferred. A reactor residence time of about 1–50 seconds is generally suitable for perchlorination and dechlorination of the acetamido moiety to the isocyanate moiety, with a residence time of about 10-20 seconds being preferred. It is necessary to have large excesses of chlorine in order to suppress carbonization in the reactor. Generally speaking, a molar ratio of chlorine to organic of 15:1 to 100:1 is operable, 20:1 to 40:1 being preferred.

While a diluent is not necessary for the present reaction, it is preferred. Representative diluents or reaction media suitable for use in this process are materials which are not detrimentally reactive under the reaction conditions with chlorine, the reactants or products. Such diluents include, for example, nitrogen, carbon dioxide, dichloromethane, tetrachloroethylene, hexachlorobutadiene, chloroform, carbon tetrachloride and the like. The preferred diluents are carbon tetrachloride, chloroform, or mixtures thereof. The feed is preferably at least from about 0.5 wt. % reactant in diluent to a saturated solution. It has been found that a 5-12 wt. % solution is typically suitable.

Operating pressures are not critical and they vary from subatmospheric to somewhat superatmospheric. Atmospheric pressure is satisfactory and is preferred.

In a preferred method of carrying out the process of the present invention, an aromatic carbocyclic or N-heterocyclic acetamido reactant and diluent are first introduced into an evaporator to produce a vaporized mixture. Tubular vaporizers are generally suitable, but a wiped film vaporizer or a reboiler type of evaporator may be more desirable with some compounds.

The exit of said vaporizer is maintained at a temperature at which rapid vaporization of the mixture occurs, usually about 25°-100°C. above the boiling point of the organic reactant.

For efficient operation it is necessary that the rate of reactant and diluent introduction and/or temperature of the evaporator be maintained so as to completely vaporize the reactant compound and maintain it in the vaporized state. It has been noted that incomplete vaporization results in decreased yield of the desired perchlorinated isocyanate. The mixed vapors are conducted from the evaporator and rapidly and turbulently mixed with gaseous chlorine. Preferably, this mixing occurs just prior to entry into a chlorinating reactor in which the resulting gaseous mixture is subjected to a turbulent flow under the temperature and time conditions set forth above. Ordinarily, an inlet vapor velocity of about 2500 to 4000 centimeters per second has been found to be satisfactory. The reactor is preferably insulated to permit the reaction to take place under adiabatic conditions. Alternatively, non-adiabatic conditions can be employed wherein conventional heat exchange techniques are employed to maintain the reaction temperatures, making appropriate adjustments in the heat capacity of the reaction mixture by regulating the proportion of diluent employed.

The actual mixing of the vaporized reactants can be accomplished in a nozzle which in turn injects the mixture into the chlorinating reactor. Alternatively, the mixed vapors of the organic reactant and diluent in chlorine may be simultaneously but separately introduced into the reactor; in such a case, for optimum yields, the chlorine must be jetted-in close to the point of introduction of the reactant and, in such a manner, insure very rapid mixing and turbulent flow of the reactants. For reactants difficult to vaporize, a solution or slurry may be atomized and sprayed directly into the reactor.

The vapors passing from the reactor are cooled or quenched to separate (a) a liquid mixture comprising perchlorinated isocyanates, diluent and unreacted or partially reacted starting materials from (b) gaseous mixture comprising chlorine and hydrogen chloride by-product.

The liquid mixture may be fractionally distilled to recover the desired product in substantially pure form or may be cooled to precipitate the product which is then recovered by conventional methods, such as filtration. The product, whether recovered by distillation or by precipitation and filtration, may then be further purified, if desired, by methods well known to those skilled in the art.

Any suitable reactor may be employed and, since the reaction is exothermic, strong heating is required only at the initiation of the reaction. Thereafter, input is only necessary to compensate for heat loss to the environment. The inlets, outlets and interior surfaces of the reactor must be of materials which resist corrosive attack by chlorine and hyrogen chloride at high temperatures. Thus, for example, such surfaces may be nickel, carbon, or a silicate glass. In practice it has been found that thermally resistant, high silicate glass such as Vycor brand is satisfactory.

As is well known, isocyanates may undergo additional reactions with active hydrogen compounds, like alcohols, amines, mercaptans, hydrazines, and the like. One may suitably convert the instant isocyanate into the carbamate, etc., either before or after purification from the previous chlorination step. The resulting derivative may then be isolated by known techniques.

SPECIFIC EMBODIMENTS

In order to illustrate the process of this invention, an apparatus was prepared consisting of a cylinder of Vycor high-silicate glass (8.3 centimeters in diameter and 41.5 centimeters in length) which was tapered to inlet and outlet tubes and fitted with electrical heating coils and insulation to serve as a reactor having a capacity of about 2.25 liters. The outlet end of said reactor was connected to a cooled collection vessel which was vented through a reflux condenser to an acid-gas recovery system.

The inlet tube ended in a nozzle projecting about 2.5 centimeters into the reactor and having an opening into the reactor about 2.5 millimeters in diameter. Inside the nozzle was a small concentric tube for chlorine introduction, said tube ending about 2.5 centimeters upstream from the nozzle opening. The upstream end of the inlet tube was connected to an electrically heated vaporizer/preheater tube used for vaporizing the reactant and the diluent.

In practice, then, a solution of from about 5.8 to 10 wt. % of the organic in $CCl_4$ or $CHCl_3$ was forced under pressure from the feed reservoir through a rotameter into the vaporizer/preheater tube, said tube having an exit temperature of from about 315° to 380°C. The hot feed vapor was then forced into the nozzle where it was mixed with chlorine which had passed through another rotameter. The mixed gaseous reactants were then jetted through the nozzle orifice into the reactor, the hot effluent gases being trapped in two consecutive dry ice/dichloromethane traps. The crude product was then placed under partial vacuum to remove practically all the free excess chlorine. For convenience sake an active hydrogen compound (alcohol, amine, mercaptan, etc.) was added to the product mixture to form the carbamate, etc. (as indicated in Table II), and it was then concentrated on a hot plate to a solid residue. The residue was further purified by recrystallization to give the isocyanate derivative, and the derivative then identified by elemental analysis, infrared and mass spectrum analysis to prove the precursor isocyanate structure.

Specific conditions and products for several runs are given in Tables I and II below:

TABLE I

VAPOR PHASE CHLORINATION OF ACETYLAMINO COMPOUNDS

| | Structure | Diluent | Feed Concentration % by wt. | Feed Rate g/m | Molar Ratio, Comp/Cl$_2$ | Vaporizer Exit, °C. | Reactor Temp. °C. | Residence Time, sec. | Yield* M% |
|---|---|---|---|---|---|---|---|---|---|
| 1. | phenyl-NH-C(=O)-CH$_3$ | CHCl$_3$ | 10.0 | 5.56 | 24/1 | 330 | 580 | 13 | 54 |
| 2. | 2-pyridyl-NH-C(=O)-CH$_3$ | CCl$_4$ | 6.66 | 3.93 | 51/1 | 315 | 570 | 16 | 70 |
| 3. | 3-pyridyl-NH-C(=O)-CH$_3$ | CHCl$_3$ | 10.0 | 4.18 | 32/1 | 375 | 565 | 15 | 47 |
| 4. | 4-pyridyl-NH-C(=O)-CH$_3$ | CHCl$_3$ | 9.67 | 3.90 | 36/1 | 50 | 565 | 15 | — |
| 5. | 2-pyrazinyl-NH-C(=O)-CH$_3$ | CHCl$_3$ | 8.79 | 5.30 | 37/1 | 315 | 550 | 12 | 53 |

*The yield of perchloroisocyanato derivative based on initial charge of acetylamino compound.

TABLE II

PROPERTIES OF ISOCYANATO REACTION PRODUCTS

I. Pentachlorophenyl-R (benzene ring with 5 Cl and R)
II. 3,5,6-trichloropyridin-2-yl with Cl and R
III. 3,5,6-trichloropyridin-4-yl with R
IV. 3,5-dichloropyridin with R
V. chloropyrazine with Cl and R

| Nucleus | —R | m.p., °C | Nucleus | —R | m.p., °C |
|---|---|---|---|---|---|
| I | —NH—C(=O)—O—CH$_2$CH$_3$ | 192–4 | II | —NH—C(=O)—OCH$_2$CH$_3$ | 141–2 |
| I | —NH—C(=O)—O—CH(CH$_3$)$_2$ | 203.5–4.5 | II | —NH—C(=O)—O—CH(CH$_3$)$_2$ | 161–2 |
| I | —NH—C(=O)—O—CH$_2$C≡CH | 192–3 | II | —NH—C(=O)—OCH$_2$C≡CH | 140–1 |
| I | —NH—C(=O)—N(CH$_2$CH$_2$CH$_3$)$_2$ | 172–6 | II | —NH—C(=O)—N(CH$_3$)$_2$ | 136.5–8.0 |
| I | —NH—C(=O)—NH—(3,4-dichlorophenyl) | 257–9 | III | —NH—C(=O)—OCH$_2$CH$_3$ | 105–640 |
| I | —NH—C(=O)—S—(CH$_2$)$_3$CH$_3$ | 133–6 | III | —NH—C(=O)—O—CH(CH$_3$)$_2$ | 129–31 |
| I | —NH—C(=O)—NH—N(CH$_3$)$_2$ | 193.5–4.5 | IV | —NH—C(=O)—OCH$_2$CH$_3$ | 179–82 |
| | | | V | —NH—C(=O)—OCH$_2$CH$_3$ | 105.5–6.5 |

TABLE II-continued
PROPERTIES OF ISOCYANATO REACTION PRODUCTS

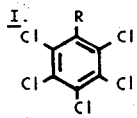

| Nucleus | —R | m.p., °C. | Nucleus | —R | m.p., °C. |
|---|---|---|---|---|---|
| | | | V | —NH—C(=O)—O—CH(CH₃)₂ | 116.5–7.5 |
| | | | V | —NH—C(=O)—NH(CH₂)₅CH₃ | 97 –8 |

I claim:

1. A process for preparing a ring-perchlorinated pyrazine isocyanate of the formula

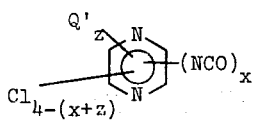

by rapidly and turbulently contacting one molecular proportion of a corresponding, prevaporized acetamido-substituted pyrazine starting material of the formula

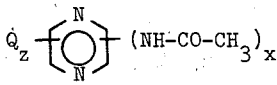

wherein $x$ is 1 or 2, $z$ is 0, 1 or 2, the sum of $x$ and $z$ is 1, 2 or 3; each Q is, independently, methyl, nitro, chloro, fluoro, bromo, iodo, cyano, methoxy, CCl₃ or CF₃ and each Q' is a fluoro, cyano or —CF₃ group originally present in said starting material as a substituent Q, with from about 15 to about 100 molecular proportions of chlorine at a temperature of from about 500° to 650°C. for from about 1 to 50 seconds.

2. The process of Claim 1 wherein said starting material is

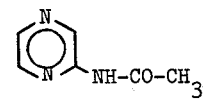

and said ring-perchlorinated pyrazine is

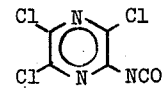

3. The process of Claim 1 wherein the starting material is mixed with a diluent prior to being vaporized.

4. The process of Claim 3 wherein the starting material is present in said mixture in an amount sufficient to -- provide -- from a 0.5 weight % solution to a saturated solution.

5. The process of Claim 1 wherein the reaction temperature is between about 550° to 600°C.

6. The process of claim 1 wherein the contact time is from about 10 to 20 seconds.

* * * * *

UNITED STATES PATENT OFFICE
CERTIFICATE OF CORRECTION

PATENT NO. : 3,957,781
DATED : May 18, 1976
INVENTOR(S) : S. H. Ruetman

It is certified that error appears in the above-identified patent and that said Letters Patent are hereby corrected as shown below:

Columns 5 and 6, Table I, Item No. 4, under heading "Vaporizer Exit, °C." number should be -- 350 --, instead of "50";

Columns 5 and 6, Table II, third line down should read across:

I   $-NH-\underset{O}{\overset{\|}{C}}-O-CH_2C\equiv CH$   192-3   II   $-NH-\underset{O}{\overset{\|}{C}}-OCH_2\equiv CH$   140-1   ;

Columns 5 and 6, Table II, sixth line down should read across:

I   $-NH-\underset{O}{\overset{\|}{C}}-S-(CH_2)_3CH_3$   133-6   III   $-NH-\underset{O}{\overset{\|}{C}}-O-CH{\overset{CH_3}{\underset{CH_3}{<}}}$   129-31   ;

Columns 5 and 6, Table II, between the fifth and sixth lines under the column heading "m.p., °C." the number "40" should be deleted;

Signed and Sealed this

Fourteenth Day of December 1976

[SEAL]

*Attest:*

RUTH C. MASON
*Attesting Officer*

C. MARSHALL DANN
*Commissioner of Patents and Trademarks*